US006895639B1

(12) United States Patent  (10) Patent No.:  US 6,895,639 B1
Bayton  (45) Date of Patent:  May 24, 2005

(54) UTENSIL GRIP SYSTEM

(75) Inventor: Robert L. Bayton, Williamsburg, VA (US)

(73) Assignee: Dining With Dignity, Inc., Williamsburg, VA (US)

( * ) Notice: Subject to any disclaimer, the term of this patent is extended or adjusted under 35 U.S.C. 154(b) by 56 days.

(21) Appl. No.: 10/446,478

(22) Filed: May 28, 2003

(51) Int. Cl.[7] ................. A45C 13/22; A45C 13/26; A47J 45/00
(52) U.S. Cl. ................. 16/430; 16/422; 15/443; 30/298; 294/25
(58) Field of Search .................. 16/430, 110.1, 16/422, DIG. 12; 15/443, 143.1, 145; 30/298, 30/232; 294/25; 81/487, 189, 177.1, 177.3; 401/6–8, 401/88; 74/558

(56) References Cited

U.S. PATENT DOCUMENTS

| 753,782 A | * | 3/1904 | Young ................. 15/443 |
| 854,019 A | * | 5/1907 | Benstead ................. 15/443 |
| 1,731,982 A | * | 10/1929 | Ortman ................. 16/435 |
| 2,206,790 A | * | 7/1940 | Read et al. ................. 30/232 |
| 4,846,710 A | * | 7/1989 | Campbell ................. 434/166 |
| 5,310,345 A | * | 5/1994 | Gershon ................. 434/166 |
| 5,695,231 A | * | 12/1997 | Hoffman ................. 294/58 |
| 6,079,758 A | * | 6/2000 | Romero et al. ................. 294/25 |
| 6,237,194 B1 | | 5/2001 | Williams ................. 16/430 |
| 2002/0096899 A1 | * | 7/2002 | Kang ................. 294/99.2 |

* cited by examiner

Primary Examiner—Chuck Y. Mah
Assistant Examiner—Michael J. Kyle
(74) Attorney, Agent, or Firm—Peter J. Van Bergen

(57) ABSTRACT

A utensil grip system is made from a strip of material defined by a first longitudinal portion terminating in a first free end, a second longitudinal portion terminating in a second free end, and a join region positioned between and coupled to each of the first and second longitudinal portions. The first longitudinal portion is shaped to define a first adjustable-size ring while the second longitudinal portion is shaped to define a second adjustable-size ring. The join region is shaped to offset the first adjustable-size ring with respect to the second adjustable-size ring. The grip region of a utensil is fixedly coupled to the join region.

20 Claims, 4 Drawing Sheets

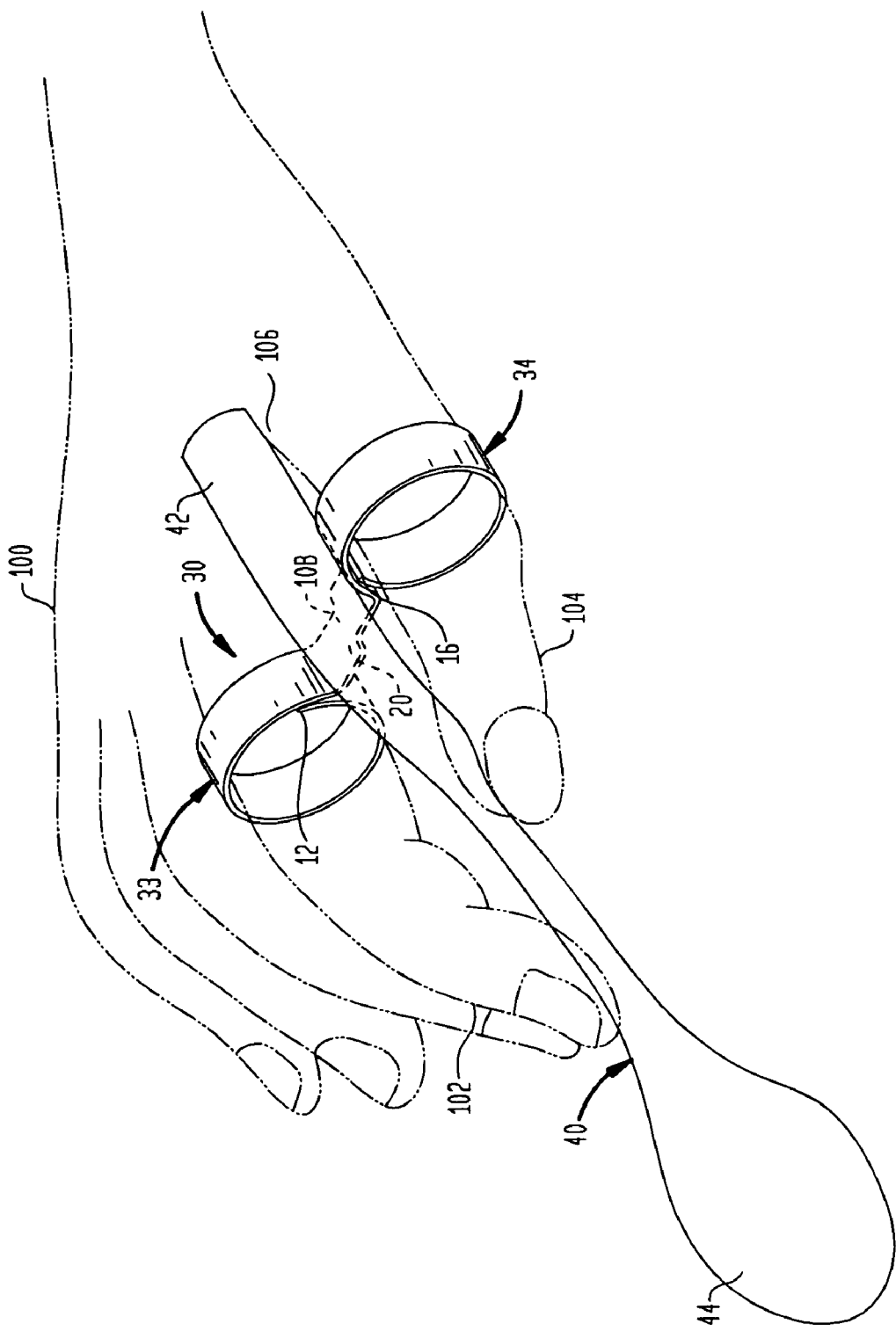

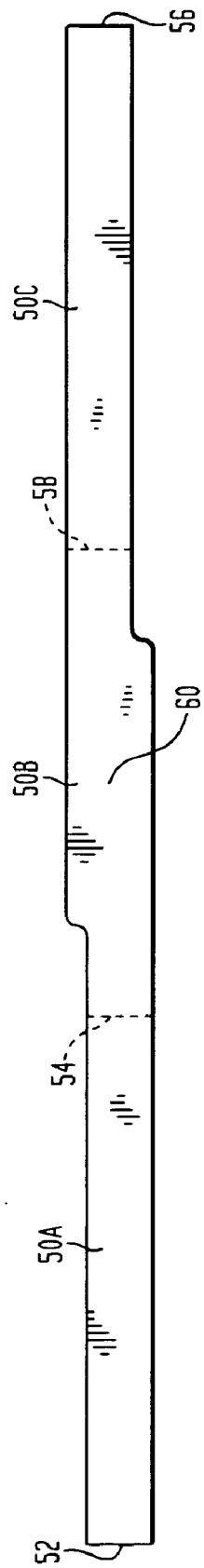
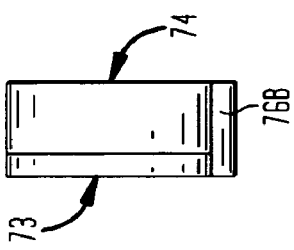
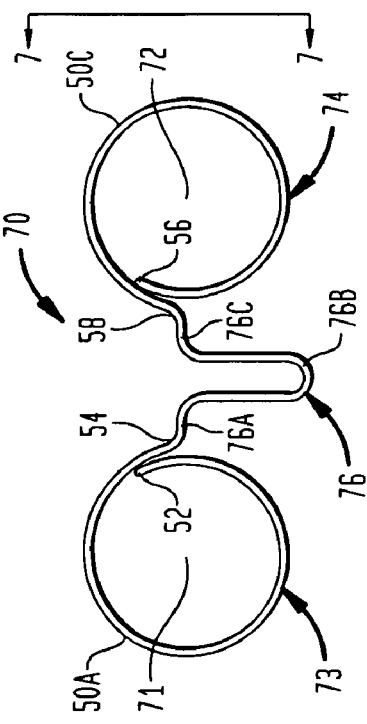
FIG. 5
FIG. 7
FIG. 6

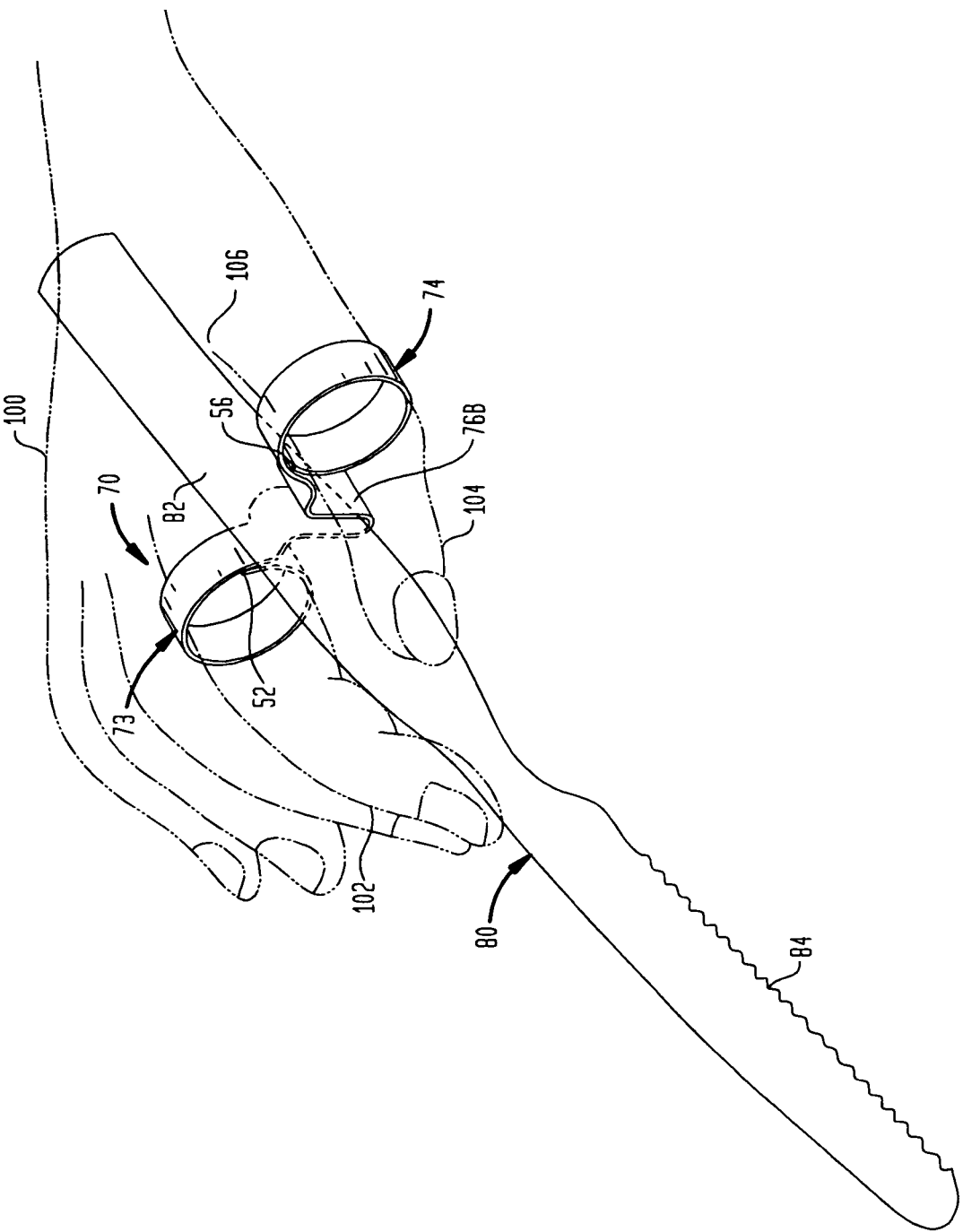

UTENSIL GRIP SYSTEM

FIELD OF THE INVENTION

The invention relates generally to utensils, and more particularly to a utensil grip system that facilitates the gripping/manipulation of a conventional utensil using one's thumb and index finger.

BACKGROUND OF THE INVENTION

The gripping and manipulation of a utensil (e.g., eating and/or cooking utensils) is an everyday task taken for granted by people without any hand or finger impairment. However, for thousands of people, cooking and eating is a challenging experience due to temporary or permanent physical conditions that limit one's hand or finger movement. Such conditions include, but are not limited to, physical deformities, paralysis or partial paralysis, arthritis, hand or finger injuries, and carpal tunnel syndrome, just to name a few.

A prior art device for assisting a physically handicapped person in the performance of a task managed by the use of one's hands is disclosed in U.S. Pat. No. 6,237,194. Briefly, this reference discloses a device that comprises a hollow member, first and second rings, an insert, and a holder. The hollow member has first and second ends and a central bore having predetermined dimensions and extending at least partially therethrough and encompassing the first end thereof. The hollow member has a plurality of apertures having threads therein. The first and second rings are attached to the hollow member via threaded engagement with the hollow member's threaded apertures. The rings are spaced apart from each other in a predetermined manner and each is dimensioned to receive one of the digits of the hand of a handicapped person. The insert has a threaded end for insertion into and threaded engagement with any one of the threaded apertures. The holder has first and second ends with the first end being dimensioned for insertion into the central bore by way of the first end of the hollow member and with the second end thereof having provisions for holding an instrument used in the performance of a task managed by the use of the hand of the handicapped person. Unfortunately, the complexities of configuring this device make such configuration thereof virtually impossible for those who have limited hand/finger mobility or dexterity. Furthermore, the device's unconventional appearance will most certainly draw attention to its use which, in turn, draws unwanted attention to a user's physical constraints.

SUMMARY OF THE INVENTION

Accordingly, it is an object of the present invention to provide a grip system for use with a utensil whereby the grip system facilitates the gripping and manipulation of the utensil.

Another object of the present invention is to provide a grip system for use with a utensil that can be easily adjusted by a user for optimum performance regardless of the individual user's hand and/or finger strength, mobility and dexterity.

Other objects and advantages of the present invention will become more obvious hereinafter in the specification and drawings.

In accordance with the present invention, a utensil grip system for use with a utensil is made from a strip of material defined by a first longitudinal portion terminating in a first free end, a second longitudinal portion terminating in a second free end, and a join region positioned between and coupled to each of the first and second longitudinal portions. The first longitudinal portion is shaped to define a first adjustable-size ring with its first free end being positioned in proximity to the join region. The second longitudinal portion is shaped to define a second adjustable-size ring with its second free end being positioned in proximity to the join region. The join region has a first end coupled to the first longitudinal portion and a second end coupled to the second longitudinal portion. The join region is further shaped to offset the join region's first end with respect to the join region's second end. As a result, the first adjustable-size ring is offset with respect to the second adjustable-size ring.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein:

FIG. 4 is a perspective view of a utensil with the grip system illustrated in FIGS. 1–3 attached thereto;

FIG. 5 is a plan view of a flat strip of material used to form another embodiment of the utensil grip system in accordance with the present invention;

FIG. 6 is a head on view of the utensil grip system formed from the strip of material shown in FIG. 5;

FIG. 7 is a side view of the utensil grip system taken along line 7—7 in FIG. 6; and FIG. 8 is a perspective view of a utensil with the grip system illustrated in FIGS. 5–7 attached thereto.

DETAILED DESCRIPTION OF THE INVENTION

Figure 3:
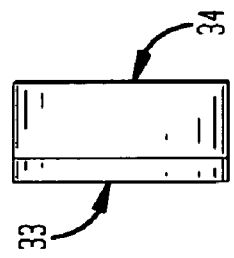
FIG. 3 is a side view of the utensil grip system taken along line 3—3 in FIG. 2.

Referring now to the drawings, simultaneous reference will be made to FIGS. 1–4 where a first embodiment of the grip system of the present invention is depicted in it's raw or pre-shaped form in FIG. 1 and after the shaping thereof in each of FIGS. 2–4. Specifically, FIGS. 2 and 3 are isolated views of the grip system whereas FIG. 4 illustrates the grip system attached to the handle or grip region of a spoon. It is to be understood that utensils other than a spoon (e.g., knife, fork, cooking utensils, etc.) can be used/combined with the grip system without departing from the scope of the present invention.

Figure 1:
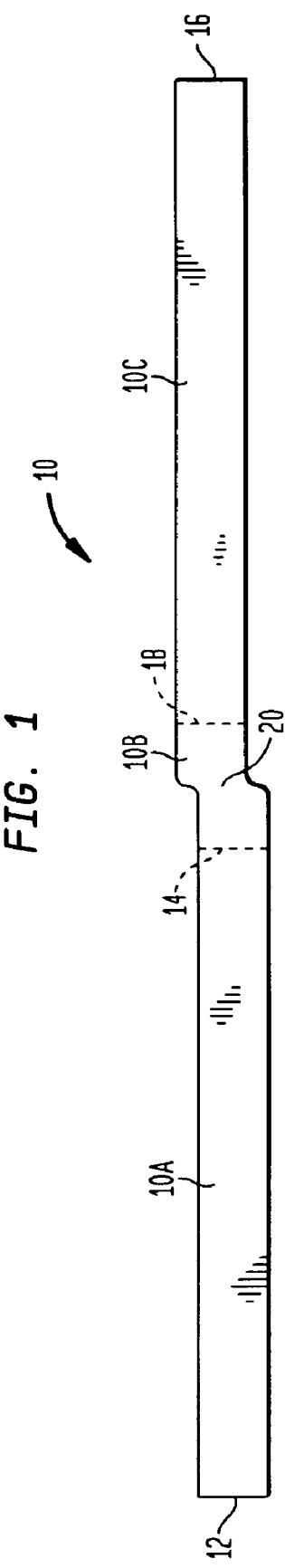
FIG. 1 is a plan view of a flat strip of material used to form one embodiment of the utensil grip system in accordance with the present invention.
Figure 2:
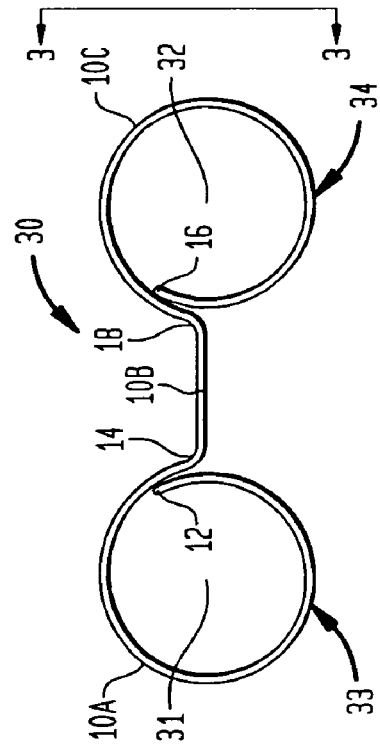
FIG. 2 is a head on view of the utensil grip system formed from the strip of material shown in FIG. 1.

In FIG. 1, a single strip of material 10 is shown in its flat or planar configuration. Strip 10 is used as the basis to form the grip system shown in FIGS. 2–4. Strip 10 is defined by a first straight-strip portion 10A, a join portion 10B, and a second straight-strip portion 10C. Straight-strip portion 10A terminates on one end thereof in a free end 12 (of strip 10) and on the other end thereof at a first end (designated by dashed line 14) of join portion 10B. Straight-strip portion 10B terminates on one end thereof in a free end 16 (of strip 10) and on the other end thereof at a second end (designated by dashed line 18) of join portion 10B. Join portion 10B is shaped at area 20 thereof to offset ends 14 and 18 with respect to one another so that straight-strip portions 10A and 10C are misaligned or offset with respect to one another along the length of strip 10.

Strip 10 is shaped to form the grip system illustrated in each of FIGS. 2–4 where the grip system is referenced generally by numeral 30. Each of straight-strip portions 10A and 1° C. is wrapped in a substantially circular fashion about respective imaginary centers 31 and 32 (shown in FIG. 2 only) to form finger rings 33 and 34 with centers 31 and 32 being approximately aligned with (flat) join portion 10B. More specifically, straight-strip portions 10A and 10C are shaped to define adjustable-size rings 33 and 34, respectively. That is, ring 33 begins at end 14 of join portion 10B and is completed by free end 12 which is positioned near end 14, but is not coupled thereto or to portion 10A. Similarly, ring 34 begins at end 18 of join portion 10B and is completed by free end 16 which is positioned near end 18, but is not coupled thereto or to portion 10C.

The shaping of join portion 10B at area 20 causes rings 33 and 34 to be offset with respect to one another as best seen in FIG. 3 where ring 33 leads ring 34 when viewed from left to right in the figure. The shaping of grip system 30 from strip 10 in this fashion is facilitated by making strip 10 from a malleable material such as metal. Since grip system 30 is contemplated for use with cooking and eating utensils, stainless steel is a good choice for strip 10 as it will withstand multiple washings without rusting or corroding. The use of a soft stainless steel facilitates a user's adjustment of grip system 30 as will be described further below. One such family of commercially-available, soft stainless steels is the 300 series of stainless steels.

Grip system 30 is fixedly coupled to a utensil 40 (e.g., by attachment means such as adhesion, welding, etc.; by integrating grip system 30 and utensil 40; etc.) as shown in FIG. 4 such as a spoon. Although this embodiment is illustrated with a spoon, it is to be understood that it could also be used with other utensils (e.g., fork, knife, various cooking utensils, etc.) without departing from the scope of the present invention. Flat join portion 10B is coupled to a central area of a grip region 42 of utensil 40 so that rings 33 and 34 are on opposing sides of grip region 42. The offset at area 20 (FIG. 1) causes ring 33 to be slightly closer to the work end 44 (e.g., the bowl in the case of a spoon) of utensil 40 than ring 34. The approximate alignment of centers 31 and 32 (of rings 33 and 34) with join portion 10B means that grip region 42 is also approximately aligned with centers 31 and 32.

Use of grip system 30/utensil 40 will now be explained with reference to FIG. 4 where a user's hand 100 is shown in phantom. Although shown and described for a right hand, the present invention is used and functions identically for a left hand. The index finger 102 is placed in ring 33 and thumb 104 is placed in ring 34. The approximate alignment of grip region 42 with centers 31/32 of rings 33/34 causes the portion of grip region 42 extending aft of grip system 30 to reside over the region 106 of hand 100 that connects index finger 102 and thumb 104.

With hand 100 positioned in rings 33 and 34, a user can adjust the shape and fit of grip system 30. Such adjustment includes accommodation for hand/finger size and/or to effect efficient use of grip system 30/utensil 40 for his particular range-of-movement and dexterity capabilities. In general, adjustment is made possible by the combination of the present invention's single strip design, adjustable-size rings, and positioning of the rings relative to the utensil's grip region. The single strip design, in addition to being simple and economical, allows a user to apply adjustment forces efficiently throughout grip system 30 to adjust the size opening of adjustable-size rings 33/34 as index finger 102 and thumb 104 are manipulated. The positioning of rings 33/34 (i.e., the offset rings 33/34, approximate alignment of grip region 42 with centers 31/32, and the positioning in the center area of grip region 42) allows the user twist rings 33/34 fore or aft through small angles to accommodate comfortable finger positioning. Specifically, through hand/finger manipulation, rings 33 and 34 can be twisted for or aft (to a comfortable position) about each end 14 and 18 of join portion 10B. Again, the single strip design of the present invention provides both the strength and flexibility to accommodate such twisting. The portion of grip region 42 that extends aft of grip system can rest and/or be acted on by region 106 (of hand 100) during the manipulation of utensil 40.

The present invention is not limited to the use of a flat join portion 10B as described above. For example, another embodiment of the present invention is shown in FIGS. 5–8. FIG. 5 depicts the embodiment in it's raw or pre-shaped form and FIGS. 6–8 depict the embodiment in it's shaped form with FIG. 8 illustrating the grip system attached to the grip region of a knife. Note that like the first embodiment, this embodiment is not limited to use with the specific utensil shown, i.e., a knife. That is, depending on one's needs/abilities, the embodiment depicted in FIGS. 5–8 may provide better positioning of, for example, a fork or spoon than the previously-described embodiment.

In FIG. 5, a flat or planar view of a single strip of material 50 is defined by straight-strip portions 50A and 50C and a join portion 50B between portions 50A and 50B. Straight-strip portion 50A terminates on one end thereof in a free end 52 and on the other end thereof at a first end 54 of join portion 50B. Straight-strip portion 50B terminates on one end thereof in a free end 56 and on the other end thereof at a second end 58 of join portion 50B. Similar to join portion 10B (FIG. 1), join portion 50B is shaped at area 60 to offset ends 54 and 58 with respect to one another so that straight-strip portions 50A and 50C are misaligned or offset with respect to one another along the length of strip 50.

Strip 50 is shaped to form grip system 70 illustrated in each of FIGS. 6–8. Specifically, rings 73 and 74 (analogous to rings 33 and 34 described above) are formed with centers 71 and 72 being approximately aligned with the center portion of a join region 76 that has been shaped from join portion 50B of strip 50. Join region 76 is defined by flat portions 76A and 76C with a U-shaped portion 76B formed therebetween. Cradled in and fixedly coupled to U-shaped portion 76B is a grip region 82 of a utensil 80 such as a knife as shown in FIG. 8. In this way, the serrated edge 84 of the knife is properly positioned for cutting and/or spreading. Use and adjustment of grip system 70/utensil 80 is the same as described above for grip system 10/utensil 40.

The advantages of the present invention are numerous. The utensil grip system described herein provides someone with limited hand dexterity or movement the means to comfortably hold and manipulate a variety of eating and cooking utensils. The design permits a user to adjust the system's size and position to suit one's hand/finger size and physical capabilities. Further, such adjustment is accomplished simply by the user once he has his fingers in the grip system. The simple design is unobtrusive thereby reducing one's self-consciousness in using same. As a result of all of the above, the present invention is an innovation that will restore self-sufficiency for a variety of individuals who currently rely on others for help in cooking and eating.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. A utensil grip system for use with a utensil, comprising:
   a single strip of material defined by a first longitudinal portion terminating in a first free end, a second longitudinal portion terminating in a second free end, and a join region positioned between and coupled to each of said first longitudinal portion and said second longitudinal portion;
   said first longitudinal portion shaped to define a first adjustable-size ring with said first free end being positioned in proximity to said join region;
   said second longitudinal portion shaped to define a second adjustable-size ring with said second free end being positioned in proximity to said join region; and
   said join region having a first end coupled to said first longitudinal portion and a second end coupled to said second longitudinal portion, said join region shaped to offset said first end with respect to said second end in a direction substantially transverse to the length of said strip wherein said first adjustable-size ring is offset with respect to said second adjustable-size ring.

2. A utensil grip system as in claim 1 wherein said join region is flat.

3. A utensil grip system as in claim 1 wherein said join region includes a U-shaped portion.

4. A utensil grip system as in claim 1 wherein said material is metal.

5. A utensil grip system for use with a utensil, comprising:
   a single strip of material defining a first adjustable-size ring, a second adjustable-size ring, and a join region positioned between and coupled to said first adjustable-size ring and said second adjustable-size ring;
   said join region positioning said first adjustable-size ring and said second adjustable-size ring to receive therethrough a thumb and index finger of a user's hand when said join region is attached to a utensil; and
   said join region having a first end coupled to said first adjustable-size ring and a second end coupled to said second adjustable-size ring, said first end being offset with respect to said second end in a direction substantially transverse to the length of said strip wherein said first adjustable-size ring is offset with respect to said second adjustable-size ring.

6. A utensil grip system as in claim 5 wherein said join region is flat.

7. A utensil grip system as in claim 5 wherein said join region includes a U-shaped portion.

8. A utensil grip system as in claim 5 wherein said material is metal.

9. A utensil grip system as in claim 5 wherein said join region is shaped to position the utensil attached thereto in approximate alignment with centers of said first adjustable-size ring and said second adjustable-size ring.

10. A utensil and grip system comprising:
    a utensil having a grip region;
    a single strip of material defined by a first longitudinal portion terminating in a first free end, a second longitudinal portion terminating in a second free end, and a join region positioned between and coupled to each of said first longitudinal portion and said second longitudinal portion;
    a portion of said join region being fixedly coupled to said grip region of said utensil;
    said first longitudinal portion shaped to define a first adjustable-size ring with said first free end being positioned in proximity to said join region;
    said second longitudinal portion shaped to define a second adjustable-size ring with said second free end being positioned in proximity to said join region; and
    said join region having a first end coupled to said first longitudinal portion and a second end coupled to said second longitudinal portion, said join region shaped to offset said first end with respect to said second end in a direction substantially transverse to the length of said strip wherein said first adjustable-size ring is offset with respect to said second adjustable-size ring.

11. A utensil and grip system as in claim 10 wherein said join region is flat.

12. A utensil and grip system as in claim 10 wherein said join region includes a U-shaped portion for receiving said grip region therein.

13. A utensil and grip system as in claim 10 wherein said material is metal.

14. A utensil and grip system as in claim 10 wherein said utensil is selected from the group consisting of a knife, a fork and a spoon.

15. A utensil and grip system comprising:
    a utensil having a grip region;
    a single strip of material defining a first adjustable-size ring, a second adjustable-size ring, and a join region positioned between and coupled to said first adjustable-size ring and said second adjustable-size ring;
    a portion of said join region being fixedly coupled to said grip region of said utensil;
    said join region positioning said first adjustable-size ring and said second adjustable-size ring to receive therethrough a thumb and index finger of a user's hand; and
    said join region having a first end coupled to said first adjustable-size ring and a second end coupled to said second adjustable-size ring, said first end being offset with respect to said second end in a direction substantially transverse to the length of said strip wherein said first adjustable-size ring is offset with respect to said second adjustable-size ring.

16. A utensil and grip system as in claim 15 wherein said join region is flat.

17. A utensil and grip system as in claim 15 wherein said join region includes a U-shaped portion for receiving said grip region therein.

18. A utensil and grip system as in claim 15 wherein said material is metal.

19. A utensil and grip system as in claim 15 wherein said join region is shaped to position said utensil attached thereto in approximate alignment with centers of said first adjustable-size ring and said second adjustable-size ring.

20. A utensil and grip system as in claim 15 wherein said utensil is selected from the group consisting of a knife, a fork and a spoon.

* * * * *